United States Patent
Fehre et al.

(10) Patent No.: US 7,942,575 B2
(45) Date of Patent: May 17, 2011

(54) UROLOGICAL X-RAY WORKSTATION WITH ORBITING X-RAY IMAGING COMPONENTS

(75) Inventors: Jens Fehre, Hausen (DE); Ralf Nanke, Neunkirchen am Brand (DE); Monika Schwarz, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 81 days.

(21) Appl. No.: 11/943,786

(22) Filed: Nov. 21, 2007

(65) Prior Publication Data

US 2009/0180586 A1 Jul. 16, 2009

(30) Foreign Application Priority Data

Nov. 22, 2006 (DE) .......................... 10 2006 055 134

(51) Int. Cl.
*H05G 1/02* (2006.01)
(52) U.S. Cl. ........................................ 378/197; 378/196
(58) Field of Classification Search .................. 378/196, 378/197, 198
See application file for complete search history.

(56) References Cited

U.S. PATENT DOCUMENTS

| | | |
|---|---|---|
| 4,894,855 A | 1/1990 | Kresse |
| 5,133,338 A | 7/1992 | Wess et al. |
| 6,775,867 B1 | 8/2004 | Kuphal et al. |
| 6,789,941 B1 * | 9/2004 | Grady ........................ 378/197 |
| 7,063,460 B2 | 6/2006 | Artmeier |
| 2003/0091153 A1 * | 5/2003 | Crain et al. .................. 378/197 |
| 2005/0053198 A1 | 3/2005 | Artmeier |
| 2008/0013691 A1 * | 1/2008 | Gregerson et al. ............ 378/198 |

FOREIGN PATENT DOCUMENTS

| | | |
|---|---|---|
| DE | 1 006 116 | 4/1957 |
| DE | 198 43 680 C1 | 2/2000 |
| FR | 2 645 007 | 5/1990 |

OTHER PUBLICATIONS

Translated abstract of Jarin et al. (FR 2645007 A1), which was published Oct. 5, 1990.*
Translated specification and claims for Jarin et al. (FR 2645007 A1), which was publihsed on Oct. 5, 1990.*

* cited by examiner

*Primary Examiner* — Chih-Cheng G Kao
(74) *Attorney, Agent, or Firm* — Schiff Hardin LLP

(57) ABSTRACT

A urological x-ray workstation has an x-ray source and an x-ray receiver that are respectively supported on device retainers of a device carrier located at the longitudinal side of a patient positioning table such that they can be positioned opposite one another and independently of one another in various positions on an orbit proceeding around a common center in a working plane oriented perpendicular to the longitudinal axis.

5 Claims, 4 Drawing Sheets

US 7,942,575 B2

UROLOGICAL X-RAY WORKSTATION WITH ORBITING X-RAY IMAGING COMPONENTS

BACKGROUND OF THE INVENTION

1. Field of the Invention

The present invention concerns a urological x-ray workstation with an x-ray source and an x-ray receiver.

2. Description of the Prior Art

Urological x-ray workstations are known for implementation of percutaneous procedures in urodiagnostics and urotherapy, in which a patient is supported on a patient positioning table between an x-ray source and an x-ray receiver, with the system axis of the x-ray system (i.e. the center axis between the x-ray source and the x-ray receiver) proceeding perpendicular to the flat side of the patient positioning table.

DE 198 43 680 C1 discloses a urological workstation in which the x-ray source and the x-ray receiver are each freely movable independently of one another in a plane that is parallel to the patient's support plane of the patient positioning table, in order to allow different diagnostically or therapeutically relevant regions of the patient to be observed or treated without having to a relocate or shift the patient. For this purpose, the x-ray source and the x-ray receiver are arranged on a column-shaped retention element that is located at a longitudinal side of the patient positioning table and that is permanently connected thereto this. The x-ray source and the x-ray radiation receiver are each mounted so that they can move in respective device retainers extending above and below the patient positioning table, extending from the columnar retention element, such that the patient positioning table is located between the x-ray source and the x-ray receiver. A longitudinal side of the patient positioning table is freely accessible for the physician in this manner.

In order to make access by the physician to therapeutically relevant regions of the patient easier in urological procedures, a urological x-ray workstation is known from DE 199 57 129 B4 in which a standing (vertical) column and retention element are provided that are not arranged centrally at the longitudinal side of the patient positioning table but rather at the head end of the table. The x-ray source and the x-ray receiver are arranged at an extension arm (boom) that can be extended in the direction of the longitudinal axis of the patient positioning table such that the x-ray source and the x-ray receiver can be displaced in the direction of the longitudinal axis, allowing the physician free access to both sides of the patient. The implementation of the surgical procedure by the physician is enabled in this manner in different positions relative to the patient.

The basic design of such a known urological x-ray workstation is illustrated in FIG. 7. In such a urological x-ray workstation, a patient positioning table 2 is located between an x-ray source 4 and an x-ray receiver 6 whose respective transmission surface 8 and reception surface 10 are arranged parallel to the flat side of the patient positioning table 2. The x-ray source 4 and the x-ray receiver 6 are arranged at respective device retainers 12 and 14 such that they can each move in a plane perpendicular to the drawing plane. The device retainers 12 and 14 are supported on a device carrier 16 that is arranged on the longitudinal side of the patient positioning table 2 at its head end and is affixed thereon. The device retainers 12 and 14 are designed such that the system axis 20 of the x-ray system formed by the x-ray source 4 and the x-ray receiver 6 can be displaced in a working plane 17 perpendicular to the longitudinal axis of the patient positioning table 2. This working plane 17 is spaced from the device retainer 16 so that the physician has free access to both sides of the patient positioning table 2 in the region of this working plane 17.

A urological treatment device 63, such as the focused shockwave or ultrasound emitter of a lithotripsy system, is schematically shown.

For therapeutic or diagnostic reasons, it is often required for the x-ray radiation to strike a patient at an angle, i.e. the system axis 20 of the x-ray system formed by the x-ray source 4 and the x-ray receiver 6 proceeds at a slant relative to the sagittal median plane 22 of the patient 18. In order to enable such an angled irradiation in the known x-ray workstations, the patient 18 is therefore supported at an angle with a support aid 24 (for example a gel pillow) in such a manner that the required angled irradiation can be achieved with an x-ray system whose system axis 20, due to design, is perpendicular to the supporting surface of the patient positioning table 2. Such an angled patient positioning is complicated and imprecise and requires the placement of supporting aids, such that a rearrangement of the patient that would be desirable during the examination or the procedure, from a therapeutic or diagnostic view into a better position, is in many cases not done because it would be too cumbersome. Moreover, the uncomfortable angled support of the patient can cause increased instability of the patient's position.

SUMMARY OF THE INVENTION

An object of the present invention is to provide a urological x-ray workstation of the aforementioned type with which it is possible to generate x-ray images with x-rays striking at an angle other than 90° relative to the median plane of the patient without an angled support of the patient being required.

This object is achieved according to the invention by a urological workstation having an x-ray source and an x-ray receiver that are respectively supported on a device retainer of a device carrier located on the longitudinal side of a patient positioning table, with the x-ray source and the x-ray receiver being supported such that they can be positioned opposite one another and independently of one another in various positions on an orbit (circular path) proceeding around a common center in a working plane oriented perpendicularly to the longitudinal axis of the patient positioning table.

The generation of x-ray exposures in which the x-rays traverse the body of a patient at an angle relative to said body's sagittal median plane is possible in this manner without an unstable angled positioning of the patient having to ensue. Since only an adjustment of components of the x-ray system is required for adjustment of the irradiation angle of the x-rays, the urologist can effect fine adjustments and corrections with little effort during the procedure or during the diagnosis. This makes both an optimization of the quality of the x-ray images and the implementation of an image-aided procedure easier for the urologist.

In the context of the present invention, the x-ray source and the x-ray detector can be positioned independently of one another when they are not rigidly mechanically connected with each another (i.e. they are not mechanically forcibly coupled) such that they can be displaced into different positions on the orbit independently of one another due to their mechanical support. In other words, in the context of the invention, they can also be positioned independently of one another even though in practice this movement or displacement ensues simultaneously via an activation of corresponding drive combinations.

In a further embodiment of the invention, the working plane is spaced from the device carrier (which can be located at the head end of the patient positioning table). A symmetrical patient access is enabled by this measure, meaning that the physician has free access to the diagnostically or therapeutically relevant region of the patient in the working plane on both longitudinal sides of the patient positioning table, which is not possible with a conventional C-arm x-ray system due to design.

DESCRIPTION OF THE PREFERRED EMBODIMENTS

Figure 1:
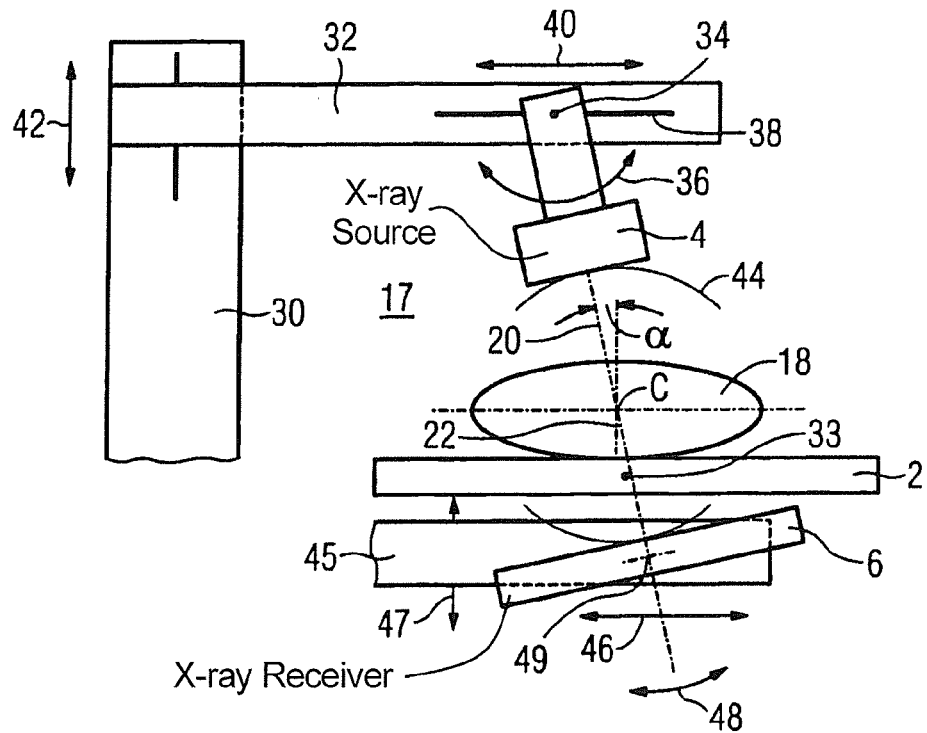
FIGS. 1 and 3-6 respectively, show schematic representations of a urological x-ray workstation according to the invention as seen in the direction of the longitudinal side of the patient positioning table.

As shown in FIG. 1, the urological x-ray workstation, like the x-ray workstation known from DE 199 57 129 B4 (the disclosure of which is incorporated herein by reference), has a device carrier 30 that is arranged at a longitudinal side of the patient positioning table 2 at its head end. The x-ray source 4 is arranged on a device carrier 32 that overhangs in the direction towards the patient positioning table 2. The x-ray source 4 can pivot in the direction of the double arrow 36 around bearing axis 34 that is parallel to the longitudinal axis 33 of the patient positioning table 2 (i.e. perpendicular to the drawing plane and to the working plane 17). The x-ray source 4 is supported on the device retainer 32 by a rail 38 proceeding transversely to the longitudinal axis 33 of the patient positioning table 2, such that the x-ray source 4 can be displaced in the direction of the double arrow 40 (i.e. perpendicularly to the longitudinal axis 33 of the patient positioning table 2), such that it can be moved linearly in the working plane 17. In addition to this, the x-ray source 4 is supported so as to be height-adjustable in the direction of the double arrow 42 either on the device retainer 32 itself or, as shown in the exemplary embodiment, by a vertical displacement capability of the device retainer 32 in the working plane 17. Movement of the x-ray source along a circular arc or an orbit 44 in the working plane 17, parallel to the drawing plane and perpendicular to the longitudinal axis 33 of the patient positioning table 2, is enabled in this manner. The center C of the orbit 44 is stationary relative to the patient positioning table 2 and, in the shown example, is located above the patient positioning table 2 and at a distance from the support axis 34. In other words, the support axis 34 and rotation axis of the orbit 44 do not coincide.

Such a combined linear and pivoting movement is also implemented by the x-ray receiver 6 supported in an analogous manner on a protruding device retainer 45 (indicated only schematically), such that the transmission surface 8 of the x-ray source 4 and the receiving surface 10 of the x-ray receiver 6 are oriented parallel to one another in a working position, and their center normals forming the system axis 20 coincide. This combined linear and pivoting movement of the x-ray receiver 6 is illustrated by the double arrows 46, 47 and 48 (pivot movement around axis 49). The x-ray source 4 and the x-ray receiver 6 are respectively positioned on the orbit 44 around the common center (isocenter) C in this manner, meaning that the system axis 20 is panned around the center C.

The x-ray source 4 and the x-ray receiver 6 thus can be moved into the respective working positions either synchronously (simultaneously) or asynchronously (successively) by movements ensuing independently of one another.

In the working position shown in FIG. 1, the x-ray radiation the patient 18 propagates slanted at an angle $\alpha$ other than 90° relative to the sagittal median plane 22 of the patient 18. Of course, conventional operation with $\alpha=90°$ is also possible.

Figure 2:
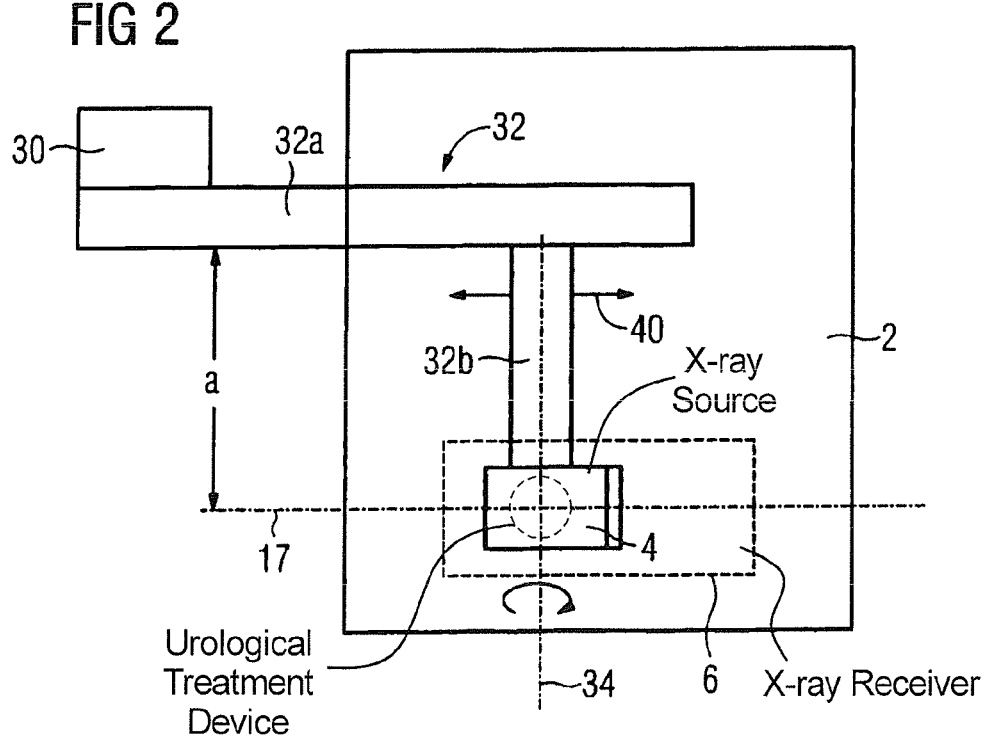
FIG. 2 is a plan view of the x-ray workstation from above, likewise in a schematic representation.

In the plan view according to FIG. 2, can be seen that the device retainer 32 is formed by a transverse carrier 32a extending transversely to the longitudinal side of the patient positioning table 2, on which transverse carrier 32a a longitudinal carrier 32b is arranged such that it can be displaced. On the free end of the longitudinal carrier 32b, the x-ray source 4 is arranged such that it can pivot. The working plane 17 perpendicular to the drawing plane is thereby located at a distance a from the device carrier 30 arranged at the head end of the patient positioning table 2, such that the physician has free access to the patient in this working plane 17 on both sides of the patient positioning table 2.

Figure 3:
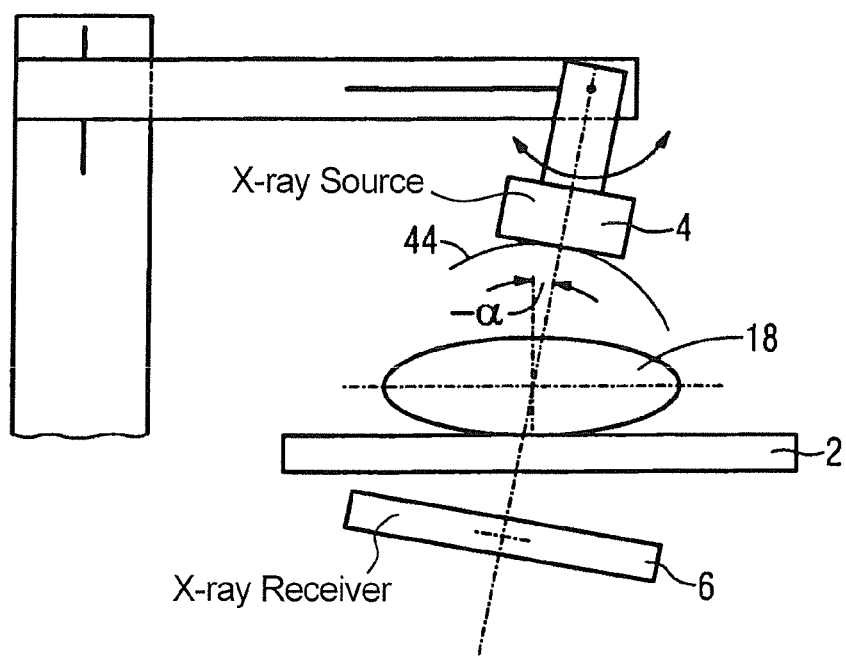

FIG. 3 shows the urological workstation according to FIGS. 1 and 2 in a working position in which the x-ray source 4 and x-ray receiver 6 are moved into an angle position $-\alpha$ on the orbit 44 relative to FIG. 1.

Figure 4:
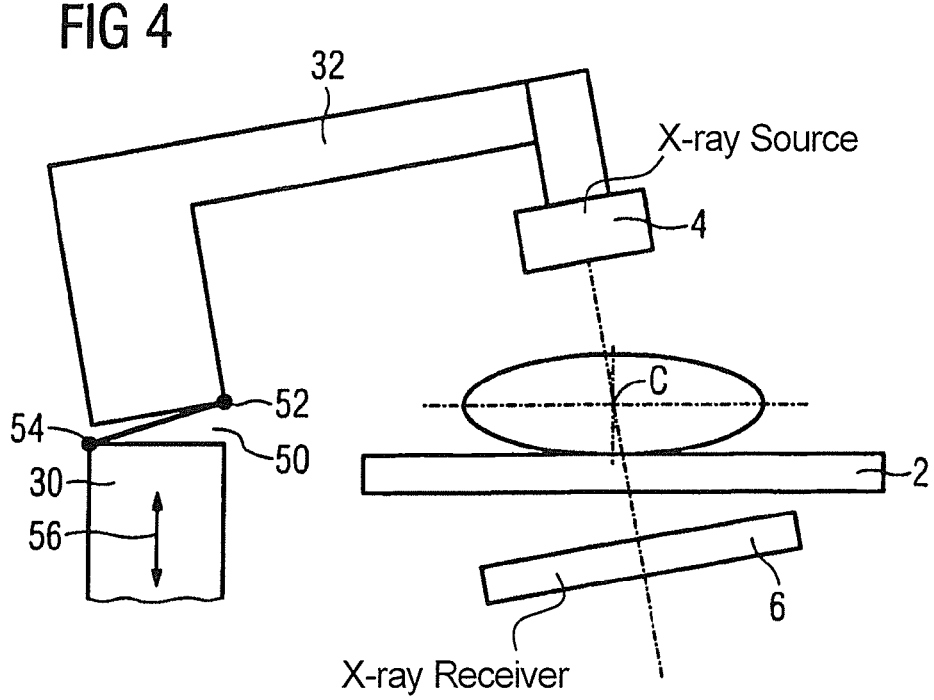
Figure 5:
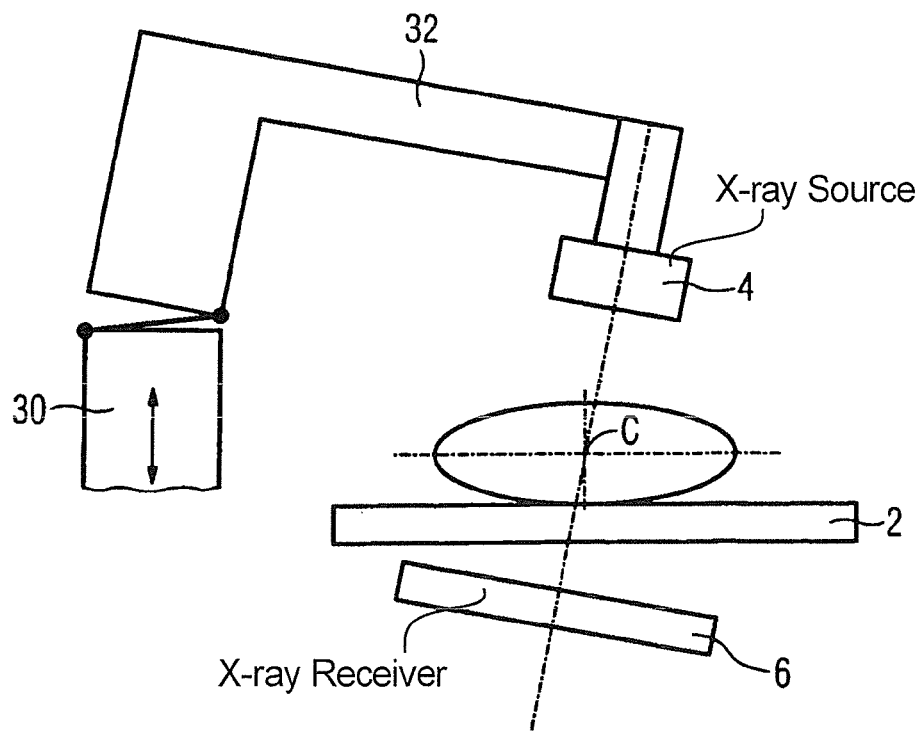

In the exemplary embodiments according to FIGS. 4 and 5, the spatially variable support of the x-ray source 4 is achieved by a hinged joint 50 with two hinge axes 52 and 54, with which the device retainer 32 is supported on the device carrier. In order to enable an orbital movement of the x-ray source 4 around a center C in this manner, an additional height adjustment of the device carrier 30 is provided that is illustrated by a double arrow 56. In the same manner, the x-ray receiver 6 also executes a synchronous movement with the x-ray source 4 via a device retainer supported on the device carrier 30 with a hinge joint. In this exemplary embodiment, as in the two preceding exemplary embodiments, the x-ray source 4 and the x-ray receiver 6 can also be forcibly mechanically coupled, or can be moved synchronously (simultaneously) or asynchronously (successively) into the respective working positions via movements ensuing independently of one another.

Figure 6:
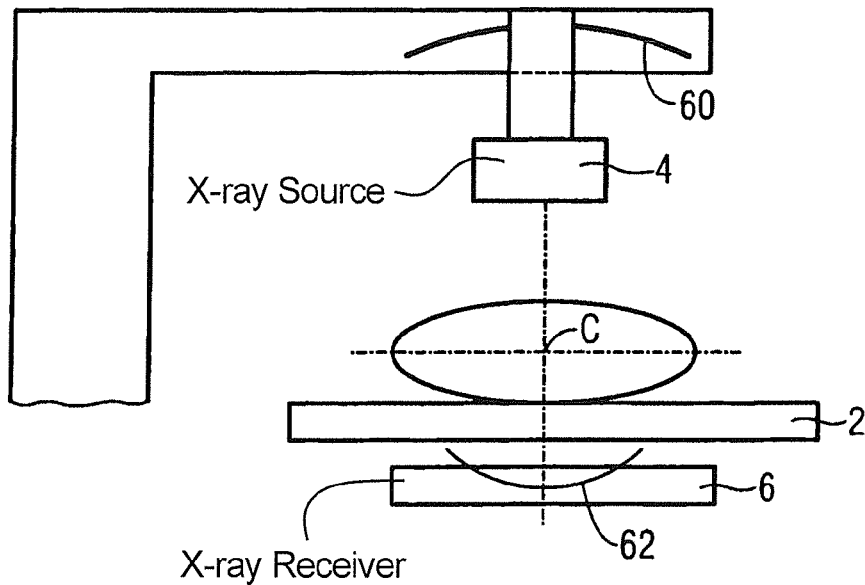
Figure 7:
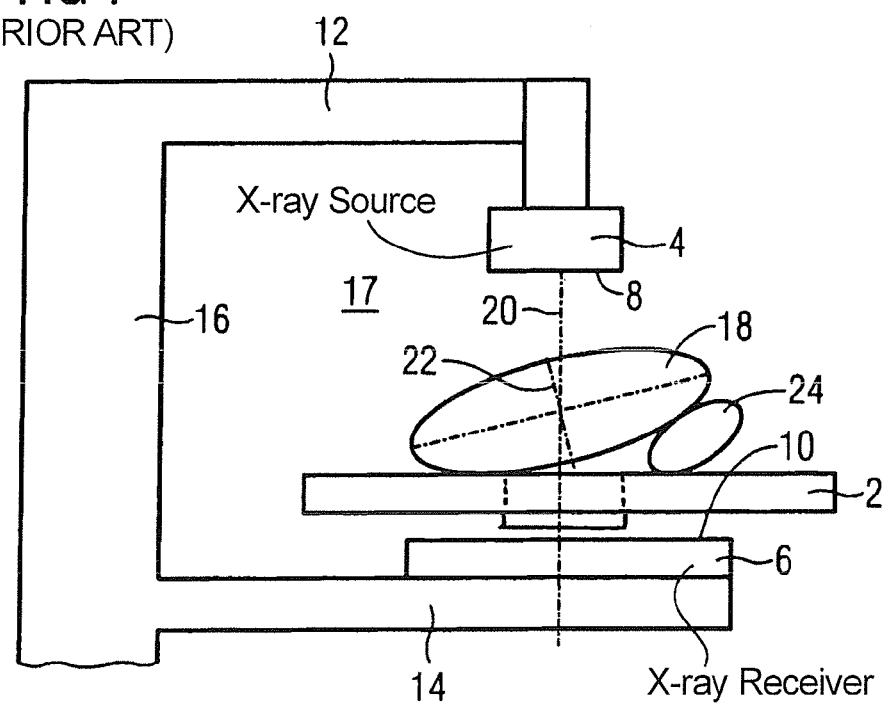
FIG. 7, as described above, is a simplified, schematic representation of a urological x-ray workstation according to the prior art with a patient supported at an angle on the patient positioning table.

In the exemplary embodiment according to FIG. 6, both the x-ray source 4 and the x-ray receiver 6 are supported along a circular arc-shaped rail segments 60 and 62, respectively. The radius center points of the rail segments 60 and 62 coincide and enable a circular movement of the x-ray source 4 and the x-ray receiver 6 around the center C.

As an alternative to the exemplary embodiments presented in the figures, it is possible to arrange both the x-ray source 4 and the x-ray receiver 6 at the respective free ends of a multi-axis robot arm. Moreover, mechanical embodiments for the movement of the x-ray source 4 and the x-ray receiver 6 that are different from one another can also be realized. For example, the spatial variability of the x-ray receiver 6 according to FIG. 5 can be combined with the spatial variability of the x-ray source 4 according to FIGS. 1 through 4.

Although modifications and changes may be suggested by those skilled in the art, it is the intention of the inventors to embody within the patent warranted hereon all changes and modifications as reasonably and properly come within the scope of their contribution to the art.

We claim as our invention:

1. A urological workstation comprising:

a patient positioning table configured to receive a patient thereon in a position allowing physician-access to anatomy of the patient for a urological procedure, said patient positioning table having a longitudinal axis;

an x-ray imaging system comprising an x-ray source and an x-ray receiver that generates an x-ray image of said patient in said position on said patient positioning table for said urological procedure; and a device carrier having respective device retainers at which said x-ray source and said x-ray receiver are mounted opposite each other with said patient table and the patient thereon between said x-ray source and said x-ray receiver, said device carrier being located at a longitudinal side of said patient positioning table and allowing said x-ray source and said x-ray receiver to be positioned opposite each other, on opposite sides of said patient positioning table, independently of each other in a plurality of positions during said urological procedure along an orbit that proceeds around a common center between said x-ray source and said x-ray receiver in a working plane that is perpendicular to said longitudinal axis, while said device carrier is entirely spaced from and does not intersect said working plane.

2. A urological workstation as claimed in claim 1 wherein said device carrier is located at a head end of said patient positioning table.

3. A urological workstation as claimed in claim 1 wherein said device retainer supports at least one of said x-ray source and said x-ray receiver to allow said at least one of said x-ray source and said x-ray receiver to be pivoted on a supporting axis proceeding perpendicular to said working plane and to be moved linearly in said working plane.

4. A urological workstation as claimed in claim 1 wherein said device carrier comprises respective circular arc-shaped rail segments at which said x-ray source and said x-ray receiver are mounted for movement in said orbit along the respective rail segments.

5. A urological workstation as claimed in claim 1 wherein said device carrier comprises a multi-axis robot arm having at least one free end, with one of said x-ray source and said x-ray receiver being mounted at said at least one free end.

\* \* \* \* \*